United States Patent [19]

Cipar

[11] Patent Number: 4,696,674

[45] Date of Patent: Sep. 29, 1987

[54] NOVEL POTATO CULTIVAR

[75] Inventor: Martin S. Cipar, Verona, Wis.

[73] Assignee: Frito-Lay, Inc, Dallas, Tex.

[21] Appl. No.: 827,373

[22] Filed: Feb. 10, 1986

[51] Int. Cl.⁴ .............................................. A01H 5/00
[52] U.S. Cl. .......................................... 800/1; 47/58;
Plt./89
[58] Field of Search ............................ Plt./89; 47/58

Primary Examiner—Robert E. Bagwill
Attorney, Agent, or Firm—Bernard, Rothwell & Brown

[57] ABSTRACT

A novel potato cultivar of the genus and species *Solanum tuberosum*, Group Tuberosum, having dark green foliage, slow but ultimately vigorous vine growth and white flowers, having tubers characterized by a pale yellow flesh color, a relatively high specific gravity, a substantially smooth round to oval shape, having resistance to a golden nematode race, and having a characteristic protein electrophoretic "fingerprint" pattern.

5 Claims, 14 Drawing Figures

NOVEL POTATO CULTIVAR

BACKGROUND OF THE INVENTION

The present invention relates to a novel potato cultivar and to tubers produced by that potato cultivar.

The potato is one of the world's most important food crops. Potatoes are currently grown commercially in nearly every state of the United States. Annual potato production exceeds 18 million tons in the United States and 300 million tons worldwide. The popularity of the potato stems mainly from its versatility and nutritional value. Potatoes can be used fresh, frozen or dried, or can be processed into flour, starch or alcohol. They contain complex carbohydrates and are rich in calcium, niacin and vitamin C.

To keep the potato industry growing to meet the needs of the consuming public, substantial research and development efforts are devoted to the modernization of planting and harvesting of fields and processing of potatoes, and to the development of economically advantageous potato varieties. Through cross-breeding of potatoes, researchers hope to obtain potatoes with the desirable characteristics of good processability, high solids content, high yield, resistance to diseases and pests and adaptability to various growing areas and conditions.

The acreage planted in potatoes has declined steadily for many years, and this decline, coupled with increasing consumption, must be offset by higher useable yields. In some areas, diseases and pests damage crops despite the use of herbicides and pesticides. The problem of the golden nematode in the United States, presently endemic to portions of New York State, is one example of the destruction to suceptible potato varieties. Potato varieties with high yields, disease resistance, and adaptability to new environments cn eliminate many problems for the potato grower and provide more plentiful and economical products to the consumers.

For the potato chip processing industry, potatoes having high solids content, good shipping qualities and good finished chip color can increase production volumes and efficiencies and product acceptability. Potato varieties which yield low-solids tubers result in unnecessary energy usage during the frying process. Moreover, as solids content increases, the oil content of fried products decreases, which is a favorable improvement.

The research leading to potato varieties which combine the advantageous characteristics referred to above is largely empirical. This research requires large investments of time, manpower, and money. The development of a potato cultivar can often take up to eight years or more from greenhouse to commercial usage. Breeding begins with careful selection of superior parents to incorporate the most important characteristics into the progeny. Since all desired traits usually do not appear with just one cross, breeding must be cumulative.

Present breeding techniques begin with the controlled pollination of parental clones. Typically, pollen is collected in gelatin capsules for later use in pollinating the female parents. Hybrid seeds are sown in greenhouses, and tubers are harvested and retained from thousands of individual seedlings. The next year the tubers are planted in the field, where extreme caution is exercised to avoid the spread of viruses and diseases. From this first-year seedling crop, several "seed" tubers from each hybrid individual which survived the selection process are retained for the next year's planting. After the second year, samples are taken for density measurements and fry tests to determine the suitability of the tubers for commercial usage. Plants which have survived the selection process to this point are then planted at an expanded volume the third year for a more comprehensive series of fry tests and density determinations. At the fourth-year stage of development, surviving selections are subjected to field trials in several states to determine their adaptability to different growing conditions. Eventually, the varieties having superior qualities are transferred to other farms and the seed increased to commercial scale. Generally, by this time, a full eight years of planting, harvesting and testing have been invested in attempting to develop the new and improved potato cultivars.

Heretofore, significant progress has been made in the development of disease-resistant, high-yield potato cultivars. There is, however, a continuing need to develop novel cultivars which combine the properties of disease resistance, resistance to pests, particularly the golden nematode, and good processability for manufacturers of potato chips and other potato products.

SUMMARY OF THE INVENTION

In accordance with the present invention, a novel potato cultivar of the genus and species, *Solanum tuberosum*, Group Tuberosum is disclosed. This cultivar has dark green foliage, slow but ultimately vigorous vine growth and white flowers and produces tubers which are characterized by a pale yellow flesh color, a good specific gravity, and a substantially smooth round to oval shape. The plants are resistant to a golden nematode race and the tubers have a characteristic protein electrophoretic pattern, as hereinafter described.

BRIEF DESCRIPTION OF THE DRAWINGS

The file of this patent contains at least one drawing executed in color to meet the requirement of 35 U.S.C. § 112. Copies of this patent with color drawings will be provided by the Patent and Trademark Office upon request and payment of the necessary fee.

DETAILED DESCRIPTION OF THE INVENTION

A novel potato cultivar of the present invention, which has been designated FL1553, has been obtained by selectively cross breeding parental clones through several generations. The immediate parents of FL1553 were a cultivar designated FL657 (♀) and Atlantic (♂), the latter being a cultivar developed by the United States Department of Agriculture. The pedigree of FL1553 includes such commercial, named cultivars as Monona, Katahdin, Wauseon and Atlantic, as well as their progenitors. These parent strains were selected for their properties of resistance to diseases or pests, good yield, solids content, chipping quality and physical appearance among other traits.

The novel potato cultivar of this invention is of the genus and species *Solanum tuberosum*, Group Tuberosum.

Figure 4:
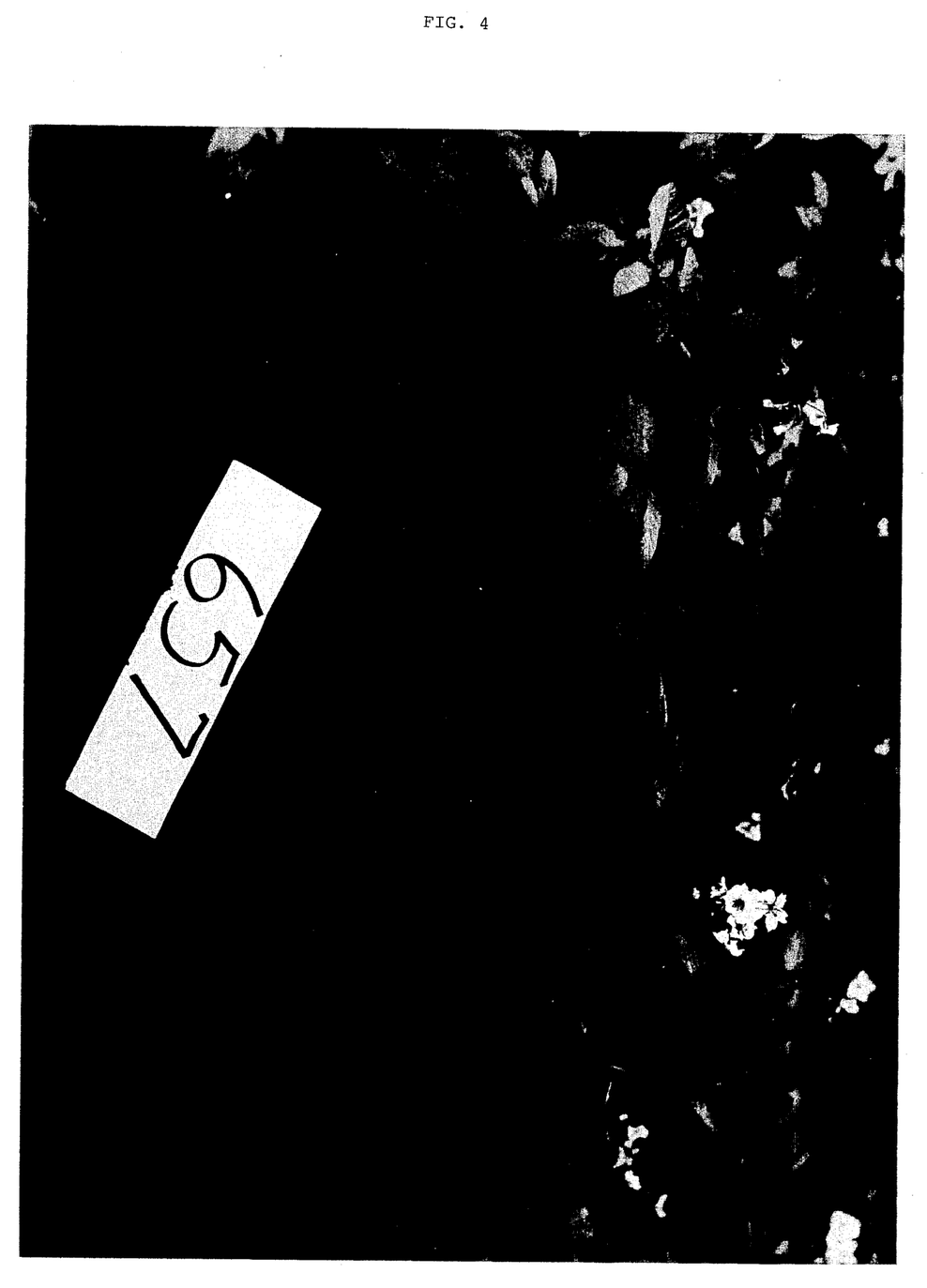
FIG. 4 is a photograph of the potato cultivar FL657.
Figure 5:
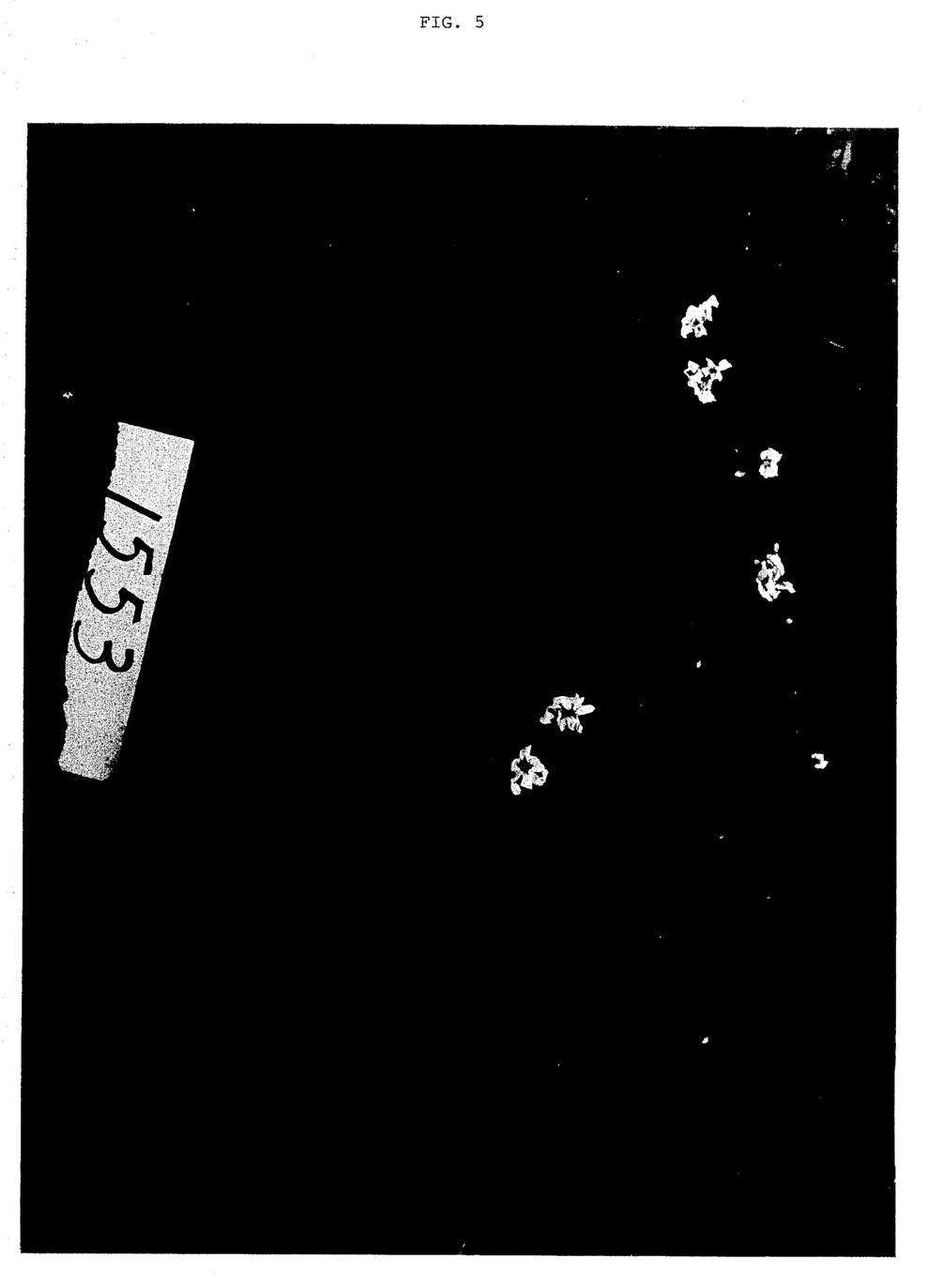
FIG. 5 is a photograph of the potato cultivar FL1553.
Figure 6:
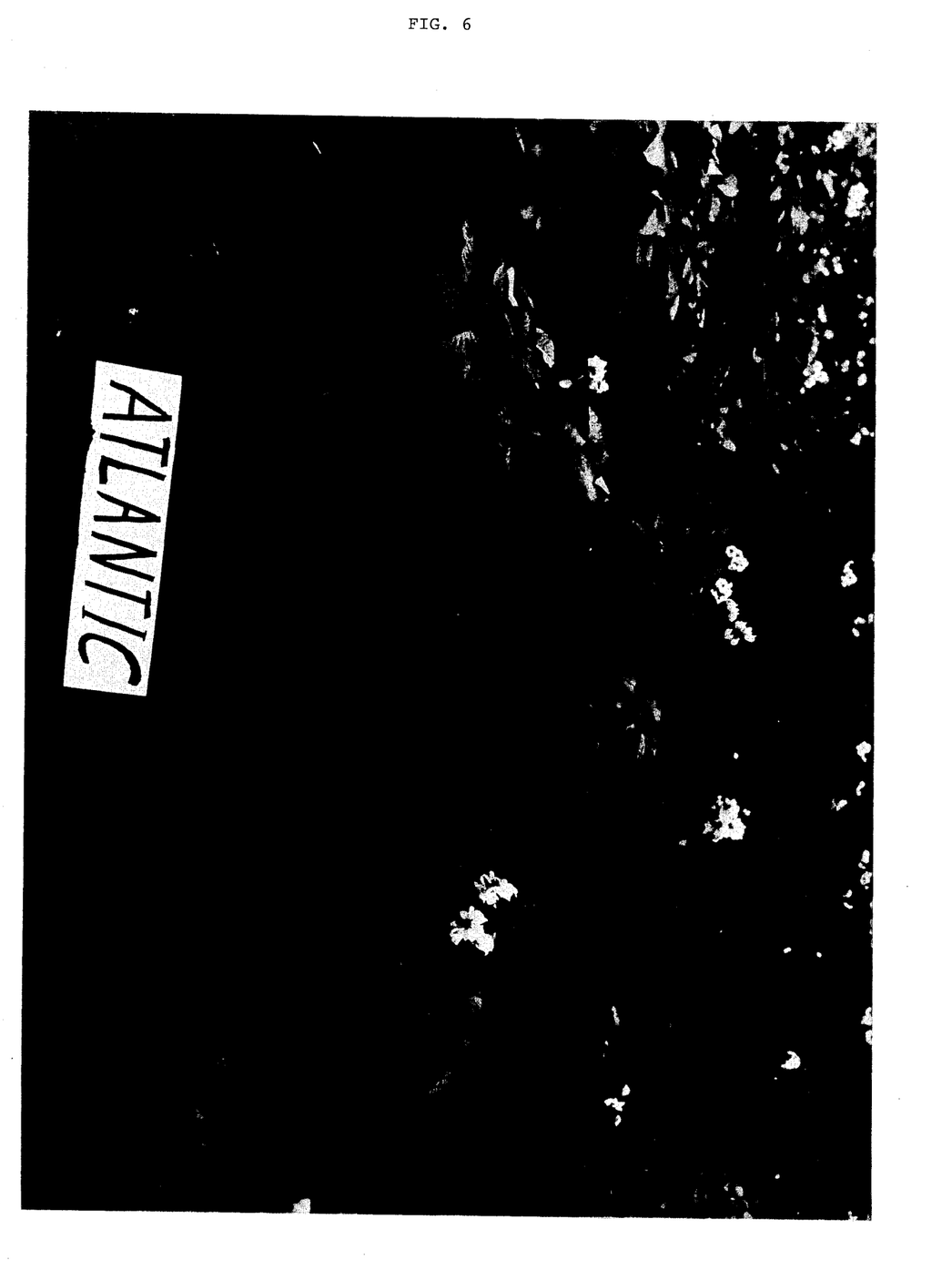
FIG. 6 is a photograph of the potato cultivar Atlantic.
Figure 7:
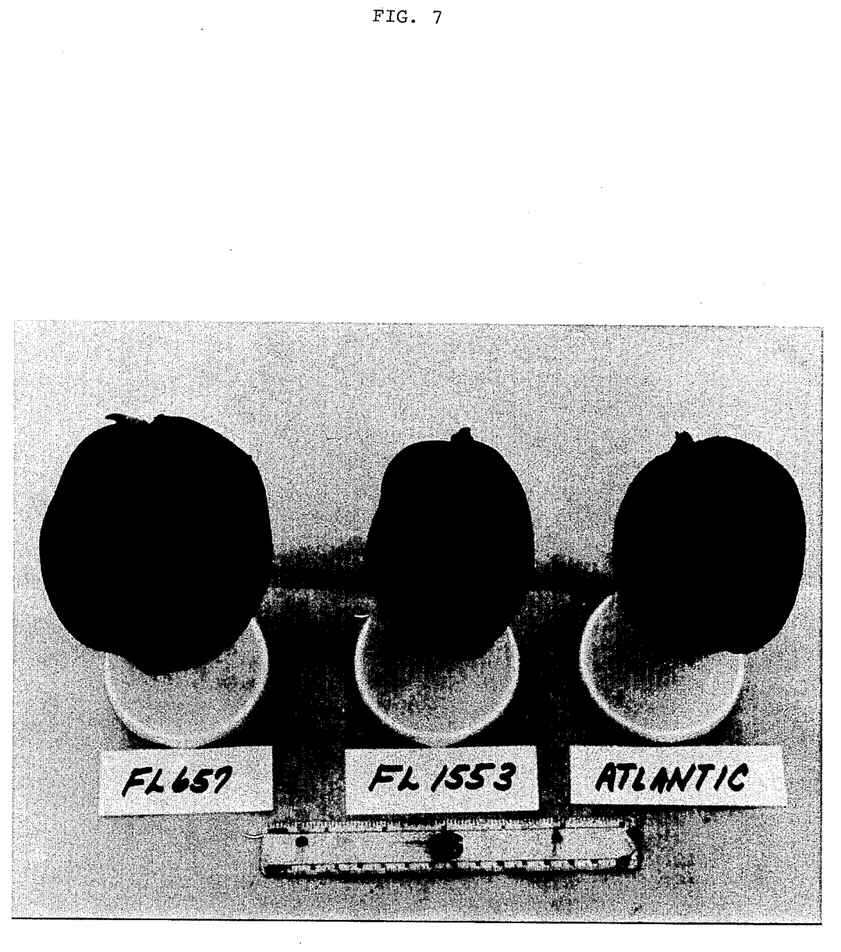
FIG. 7 is a photograph of the whole tubers from potato cultivar FL657, potato cultivar FL1553 and potato cultivar Atlantic.
Figure 8:
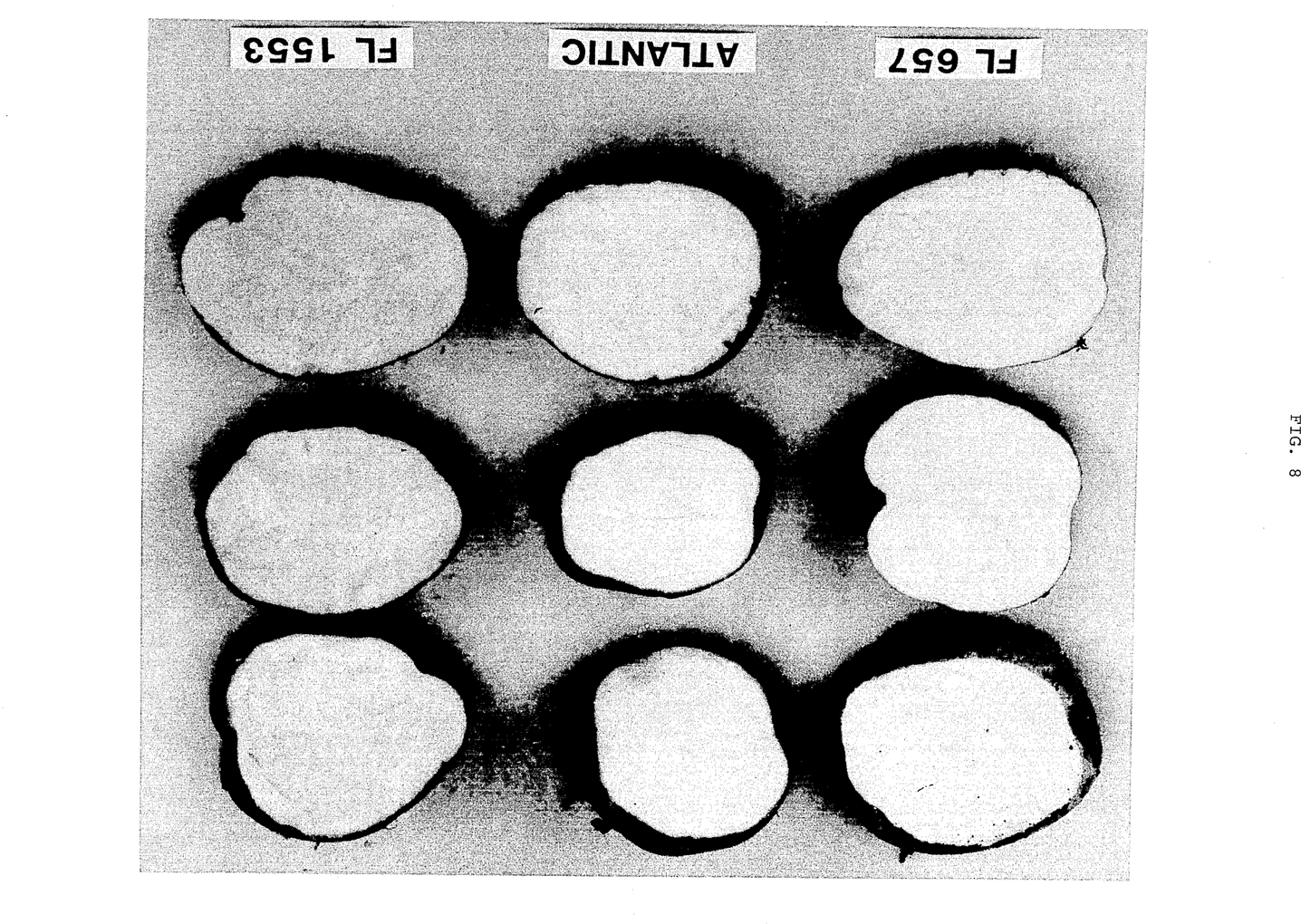
FIG. 8 is a photograph of cut tubers from potato cultivar FL657, potato cultivar FL1553 and potato cultivar Atlantic.

This cultivar has dark green foliage, as shown in FIG. 5. The foliage of the parents of FL1553 may be seen in FIG. 4 and 6. FL1553 has slow, but ultimately vigorous vine growth and white flowers and produces tubers which are characterized by a pale yellow flesh color, a good specific gravity, and a substantially smooth round to oval shape. A comparison of the size and shape of the tubers from the parent cultivars and the cultivar of this invention is shown in FIG. 7. FIG. 8 illustrates the flesh color of the cut tubers produced by the parent cultivars and FL1553. The tubers produced by this cultivar are well-suited for the production of potato chips. A characteristic feature of the tubers is their comparatively good specific gravity relative to the standard commercial variety in a production area. The specific gravity generally ranges from about 1.06 to about 1.10; however, it will be appreciated that specific gravities can vary substantially depending upon growing conditions and areas. Higher specific gravities are advantageous for chipping and other frying applications, as they reduce the total energy and time required for the frying operation. The high solids content of these tubers also reduces the frying oil content of resulting finished products, a beneficial property with respect to calorie content, shelf life, and other features.

In addition to the specific gravity of the tubers of this invention, they also have an advantageous shape for commercial operations. The tubers are relatively smooth skinned. They generally lack knobs and other protuberances, as well as deep ridges or convolutions. Accordingly, they are amenable to efficient washing and peeling operations using large-scale automated equipment. Such shapes produce a high quality product with a minimal amount of waste. The tubers are generally round to oval in shape and have a size which is suited to the manufacture of potato chips. In general, these tubers have a mean length of 8.9 centimeters (range: 6.7–11.3 centimeters); a mean width of 6.8 centimeters (range: 5.7–8.1 centimeters) and a mean thickness of 5.7 centimeters (range: 4.5–7.5 centimeters) based upon a 100-tuber sample. Of course, the size of the tubers can vary over a relatively wide range depending upon growing conditions and locations. The slightly flattened shape of the tubers is advantageous, because it facilitates alignment in the slicing apparatus.

Among the more important characteristics of the potato cultivar of this invention is its resistance to the race of golden nematode (*Globodera rostochiensis*) found in New York state. This pest has posed a serious threat to plants grown for seed and for consumption.

Other advantageous properties of the plants of the present invention include competitive yield, where adapted and the ability to grow and yield well under dryland cultural conditions. Cultivar FL1553 has adapted well to cultivation in New York state, where the golden nematode has been problematic. FL1553 has not adapted to all production areas, and the development of undesirable hollow-heart can be a concern in such areas.

In addition to the morphological characteristics and disease and pest resistances described above, the plants of this invention are characterized by their protein "fingerprint" patterns. The protein fingerprint is determined by separating tuber proteins on an electrophoretic gel under certain defined conditions. The pattern of the proteins, attributable to their differential mobilities on the electrophoretic gel, have been found to be characteristic of the particular plant involved. This pattern has thus been termed a "fingerprint." The protein fingerprinting technique has been used by different investigators to differentiate large numbers of potato varieties. See, Desborough, S. and Peloquin, S. J., *American Potato Journal*, 45, 220–229 (1968) and Desborough, S. and Peloquin, S. J., *Theoretical and Applied Genetics*, 39, 43–47 (1969). These techniques generally involve extracting proteins from the tuber and applying the extract to an electrophoretic gel (e.g., polyacrylamide). The proteins are separated electrophoretically, and peroxidase and esterase enzyme systems as well as other soluble proteins are visualized by staining techniques and the application of enzyme substrates. Electrophoretic patterns of proteins solubilized with sodium dodecyl sulfate (SDS) and esterases have been found particularly valuable in characterizing potato cultivars. The protein fingerprinting technique and patterns are described more fully in the drawings and in the examples which follow.

Potato cultivar FL1553 has been deposited with American Type Culture Collection 12301 Parklawn Dr., Rockville, Md. 20852 and given Accession Number 40202. This depository is independently maintaining the cultivar in sterile tissue culture using conventional micropropagation techniques. Plants which are genetically identical to the original deposit can be obtained by growing these tissue cultures and transplanting into greenhouses and ultimately fields.

Thus, according to the present invention a novel potato cultivar having desirable characteristics of disease and pest resistance, yield, color, specific gravity, adaptability to varying cultural conditions, and processability has been disclosed. The invention is further illustrated by the following examples which are not intended to be limiting.

EXAMPLE I

This example describes the determination of electrophoretic fingerprint patterns for proteins extracted from tubers of FL1553.

Materials

Basic Extraction Buffer
 2 g tris (hydroxymethyl)aminomethane (TRIS)
 6.6 g glycine
 0.5 g sodium metabisulfite
 q.s. distilled water to 250 ml.
 pH 8.3
SDS Extraction Buffer
 0.30 g TRIS (as pH 6.8 aq. solution)
 10 g glycerol
 5 g mercaptoethanol
 30 ml. 10% sodium dodecylsulfate (SDS)
 q.s. distilled water to 100 ml.
Basic Acrylamide Gels
 Stock Solutions:
  Stock A 48 ml 1N HCl
36.3 g TRIS
0.46 ml N,N,N',N"-tetramethylenediamine (TEMED)
q.s. distilled $H_2O$ to 100 ml.
pH 8.8–9
Stock B
  25.6 ml 1M $H_3PO_4$
  0.46 ml TEMED
  5.7 g TRIS
  q.s. distilled $H_2O$ to 100 ml.
  pH 6.9
Stock C
  30.0 g acrylamide
  0.8 g N,N'-methylenebisacrylamide
  q.s. distilled $H_2O$ to 100 ml.
Stock D
  10.0 g acrylamide
  2.5 g N,N'-methylenebisacrylamide
  q.s. distilled $H_2O$ to 100 ml.
Stock E
  riboflavin 4 mg/100 ml.
Stock G
  ammonium persulfate 0.14 g/100 ml
Basic Reservoir Buffer
  28.8 g glycine
  6 g TRIS
  q.s. distilled $H_2O$ to 1 liter
  pH 8.3
$7\frac{1}{2}$% running gels are prepared by combining the following:
  3.0 ml Stock A
  6.0 ml Stock C
  3.0 ml $H_2O$
  12.0 ml Stock G
Stacking gels are prepared by combining the following:
  1.0 ml Stock B
  1.5 ml Stock D
  0.5 ml Stock E
  1.75 ml distilled $H_2O$
SDS Acrylamide Gels
Stock Solutions
  Running Gel Buffer - 1.5M TRIS-HCl, pH 8.8
  Stacking Gel Buffer - 0.5M TRIS, pH 6.8
  12% running gels are prepared by combining the following:
    4.0 ml distilled $H_2O$
    2.4 ml Stock C (See above)
    3.5 ml running gel buffer
    100 μl 10% SDS
    20 μl 10% ammonium persulfate
    5 μl TEMED
  12% stacking gels are prepared by combining the following:
    3.1 ml distilled $H_2O$
    0.5 ml Stock C (See above)
    1.75 ml stacking gel buffer
    50 μl 10% SDS
    5 μl TEMED
  Reservoir buffer for SDS-Acrylamide gels is prepared by combining the following:
    200 ml Basic Reservoir Buffer
    20 ml 10% SDS
    q.s. distilled $H_2O$ to 2 liters
Coomassie Blue Dye Staining Solution
  454 ml 50% methanol
  46 ml glacial acetic acid
  0.125 g Coomassie Blue Dye R-250 (Pierce Chemical Co.)
  (Solution filtered through filter paper before use.)
Clearing Solution
  454 ml 50% methanol
  46 ml glacial acetic acid
Esterase Staining Solution
  2.5 ml of 1% w/v -napthylacetate in acetone
  50 mg fast blue RR salt
  q.s. 0.01M pH 7 phosphate buffer to 50 ml.

Procedure

Five grams of fresh tuber from FL1553 were cut into small cubes, and these cubes were soaked in 0.7% sodium hydrosulfite in the cold for at least 30 minutes. The cubes were rinsed thoroughly with distilled water and 1 ml of Basic Extraction Buffer was added to the cubes. This mixture was then ground to a fine slurry. The slurry was centrifuged at 16,000×g for 30 minutes and the supernatant used for electrophoresis in the $7\frac{1}{2}$% basic acrylamide gels. A portion of the supernatant was diluted 1:1 with SDS Extraction Buffer and heated to boiling and this solution was used for electrophoresis in 12% SDS gels. Slab gels were prepared in the conventional manner, using the respective Basic Acrylamide and SDS Acrylamide running and stacking gel compositions described above. Running gels were poured to within $\frac{3}{4}$ inch of the top of the gel and polymerized, and the remaining space was filled with stacking gel. Tuber protein extracts in Basic Extraction Buffer and SDS Extraction Buffer (25 μl samples) were applied to the $7\frac{1}{2}$% Basic Acrylamide Gels and the 12% SDS Acrylamide Gels, respectively. The gels were placed in conventional apparatus, and the reservoirs filled with the appropriate reservoir buffers as described above. Current was applied (60 m Amperes) and electrophoresis was run in the conventional manner. After completion of electrophoresis (as evidenced by the location of a tracking dye), gels were removed, the stacking gels removed and protein bands were visualized as follows:

Soluble Proteins

The 12% SDS Acrylamide Gel was placed in a disk and covered with Coomassie Blue Staining Solution. After color development, the gel was removed from the stain and destained by washing with the Clearing Solution until protein bands were distinct.

Esterases

Esterase enzyme patterns were visualized in the $7\frac{1}{2}$% Basic Acrylamide Gels by staining with a chromogenic substrate solution. The gel was placed in a dish and covered with Esterase Staining Solution until esterase bands were distinct.

Protein Patterns

Figure 1:
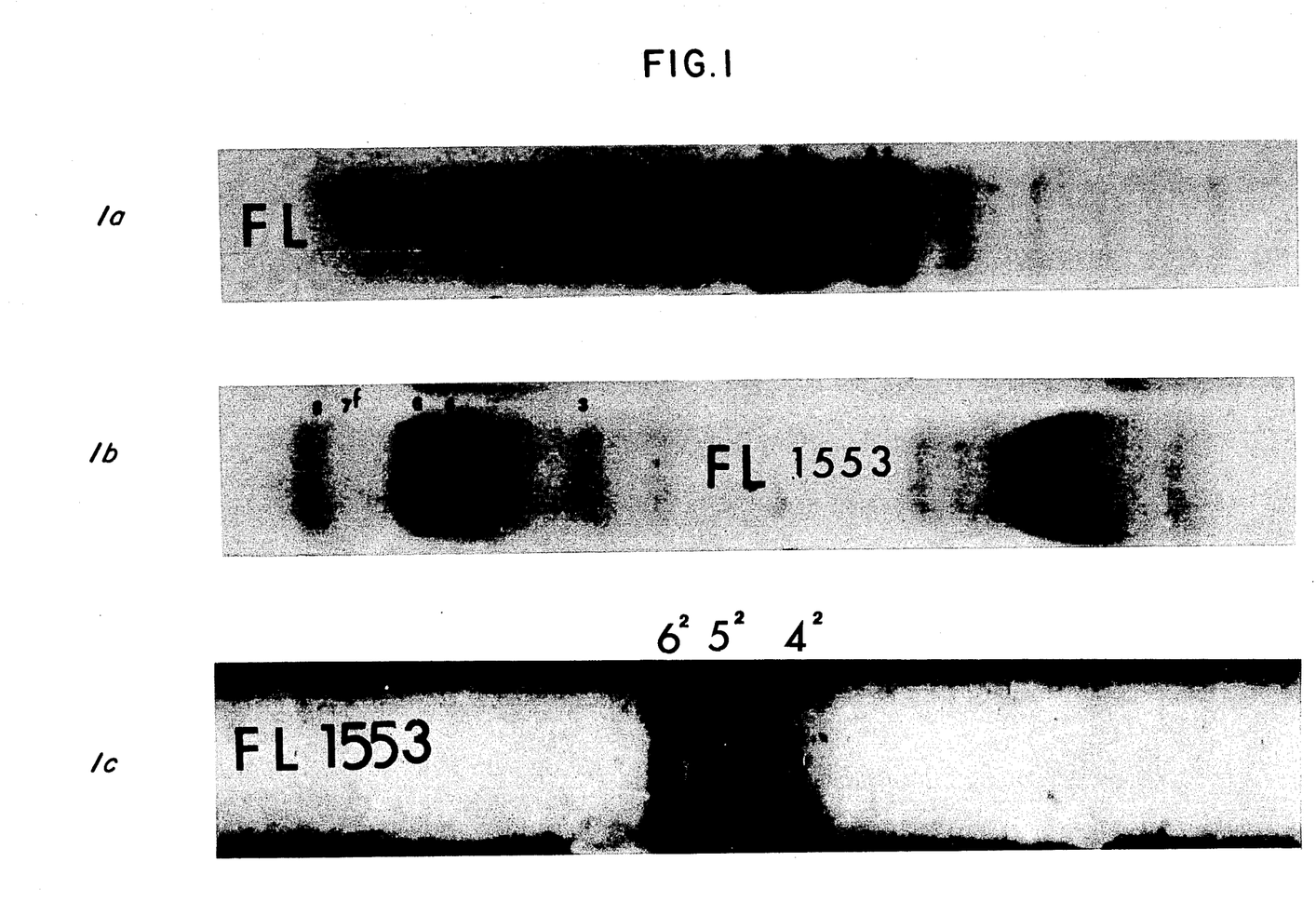
FIG. 1 is a photograph of the electrophoretic fingerprint patterns of potato cultivar FL1553.

A conventional numbering system is used for assigning locations to each soluble protein band and each esterase band visualized by the above procedures. (See Desborough, S. et al., Am. Potato J., supra and Desborough, S. et al., Phytochemistry, 6, 989–994 (1967)). Using this numbering system, the electrophoretic patterns for FL1553 soluble proteins and esterases was determined to be as follows:

SM 1257   SL 3467/8   EB $4^{25}6^2$

SM stands for soluble protein middle bands, SL stands for soluble protein lower bands and EB stands for esterase bands. Superscript "c" indicates a concentrated band, superscript "f" indicates a faint band and numerical superscripts indicate multiple band (e.g., doublet or triplet) at the indicated location. Photographs of the soluble protein middle bands (SM), lower bands (SL) and esterase electrophoresis gels of cultivar FL1553 are shown in FIG. 1a, 1b and 1c, respectively.

EXAMPLE II

Figure 2:
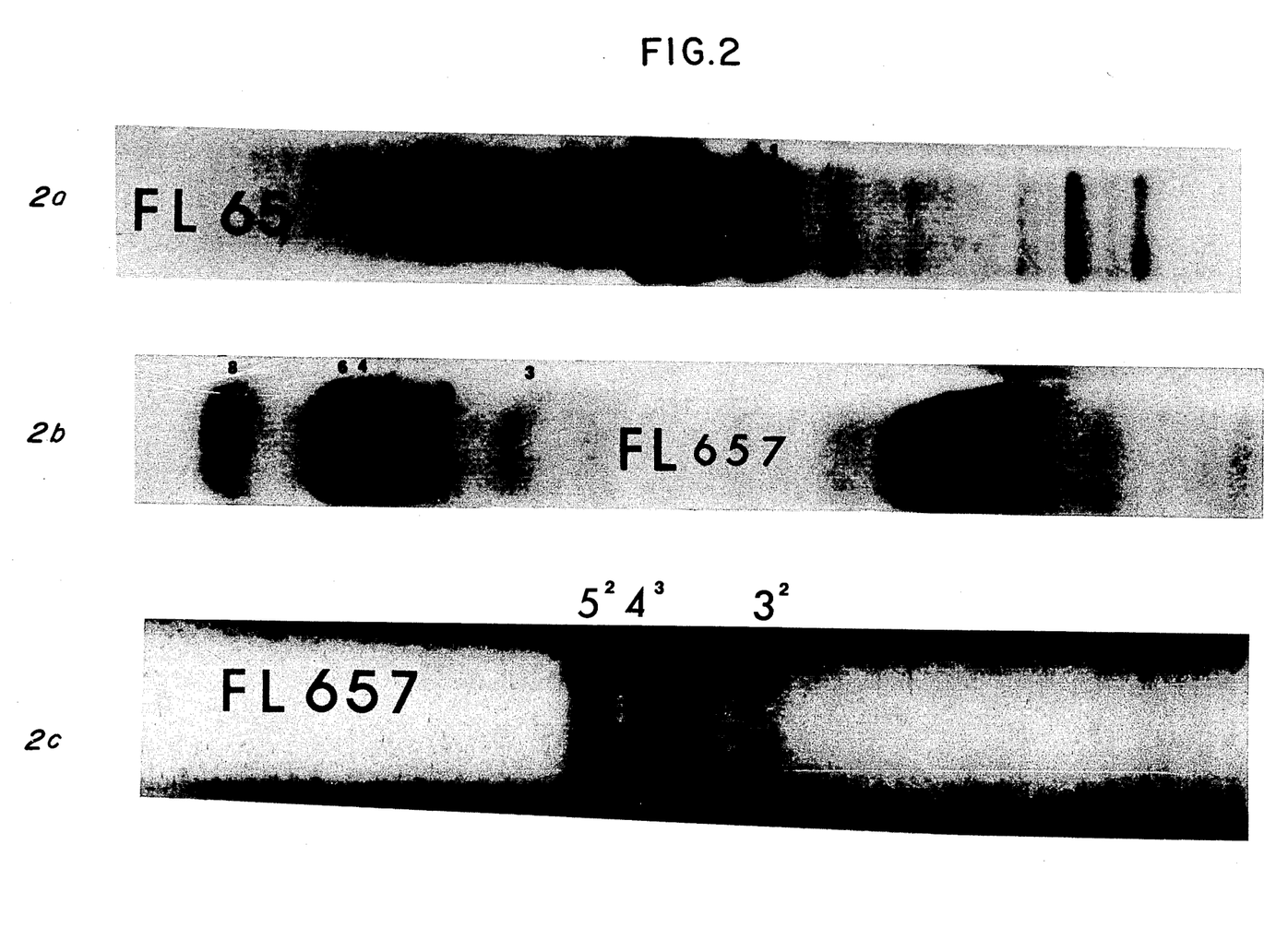
FIG. 2 is a photograph of the electrophoretic fingerprint patterns of potato cultivar FL657.
Figure 3:
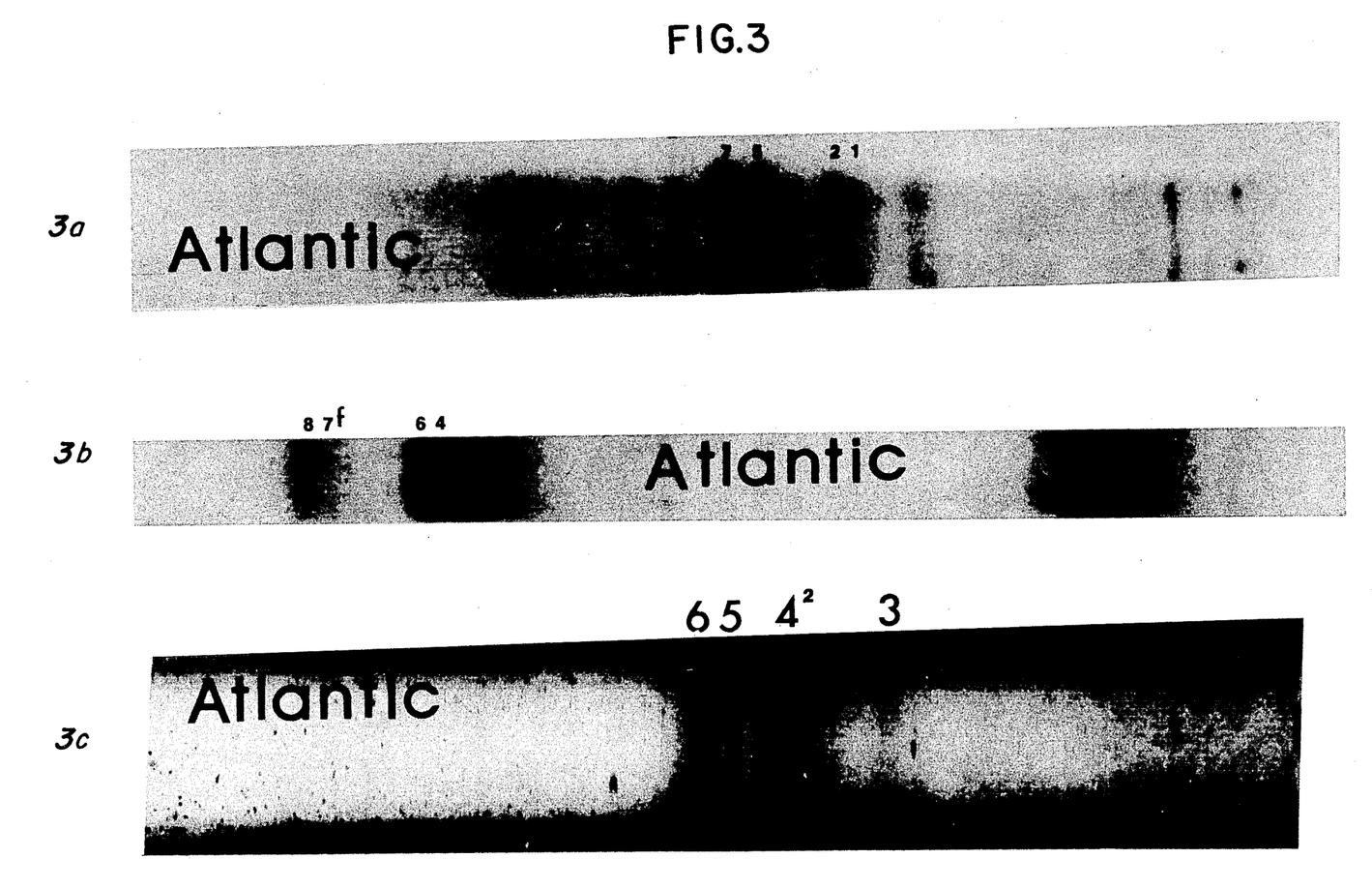
FIG. 3 is a photograph of the electrophoretic fingerprint patterns of potato cultivar Atlantic.

The procedures of Example I were repeated in all essential details to determine the electrophoretic fingerprint patterns of FL657 and Atlantic, the parents of FL1553. These patterns were determined to be:

FL 657    SM1257    SL3468    EB3$^{24}$3$^{52}$
Atlantic  SM1257    SL467/8   EB34$^2$56

Photographs of the soluble protein middle bands (SM), lower bands (SL) and esterase electrophoresis gels of cultivar FL657 are shown in FIGS. 2a, 2b and 2c, respectively. Photographs of the soluble protein middle bands (SM), lower bands (SL) and esterase electrophoresis gels of cultivar Atlantic are shown in FIG. 3a, 3b and 3c, respectfully.

I claim:

1. A potato cultivar of the genus and species *Solanum tuberosum*, Group Tuberosum, having dark green, slow-growing but ultimately, vigorous vine growth and white flowers and resistance to a golden nematode race, having tubers characterized by a pale yellow flesh color, a relatively high specific gravity, a substantially smooth round to oval shape, and having the protein electrophoretic fingerprint pattern substantially as shown in FIG. 1 of the drawings.

2. The potato cultivar of claim 1 wherein the tubers are generally oval in shape and have a length of from about 6.7 to about 11.3 cm, a width of from about 5.7 to about 8.1 cm and a thickness of from about 4.5 to about 7.5 cm, and specific gravity of from about 1.06 to about 1.10.

3. The potato cultivar of claim 1, variety FL1553, a tissue culture of which is on deposite with the American Type Culture Collection, accession number 40202.

4. A tuber produced by the potato cultivar of claim 1, 2 or 3.

5. A method for producing potatoes which comprises cultivating, under potato-growing conditions, the potato cultivar of claim 1, 2 or 3.

* * * * *